United States Patent
Dai et al.

(10) Patent No.: US 11,744,818 B2
(45) Date of Patent: Sep. 5, 2023

(54) APPLICATION OF TRANS-1,3-DILINOLEIN IN THE PREPARATION OF MEDICAMENTS FOR TREATING GASTRIC CANCER, STOMACHIC TONIC, HEALTH PRODUCTS AND FOODS

(71) Applicant: Lanzhou University, Lanzhou (CN)

(72) Inventors: Jianye Dai, Lanzhou (CN); Zheng Jin, Lanzhou (CN); Ruyun Ma, Lanzhou (CN); Yanning Zhu, Lanzhou (CN)

(73) Assignee: Lanzhou University, Lanzhou (CN)

( * ) Notice: Subject to any disclaimer, the term of this patent is extended or adjusted under 35 U.S.C. 154(b) by 64 days.

(21) Appl. No.: 17/450,845

(22) Filed: Oct. 14, 2021

(65) Prior Publication Data

US 2022/0218645 A1 Jul. 14, 2022

(30) Foreign Application Priority Data

Jan. 9, 2021 (CN) .......................... 202110026727.7

(51) Int. Cl.
*A61K 31/231* (2006.01)
*A61P 35/00* (2006.01)

(52) U.S. Cl.
CPC ............ *A61K 31/231* (2013.01); *A61P 35/00* (2018.01)

(58) Field of Classification Search
CPC .............................. A61K 31/231; A61P 35/00
See application file for complete search history.

(56) References Cited

PUBLICATIONS

Paris et al. (Journal of Medicinal Chemistry (1980), 23(1), 9-13). Abstarct.*

* cited by examiner

*Primary Examiner* — Bruck Kifle
(74) *Attorney, Agent, or Firm* — AVEK IP, LLC

(57) ABSTRACT

Some embodiments of the disclosure provide new uses of trans-1,3-dilinolein as medicaments and food. In an embodiment, an application of trans-1,3-dilinolein in the preparation of stomachic tonic and an application thereof include the preparation of medicaments for treating gastric cancer. Cell experiments show that trans-1,3-dilinolein promotes the proliferation of human gastric mucosal epithelial cell line GES-1 under normal oxygen and hypoxic conditions and it has concentration-dependent killing effect on human gastric cancer cell line HGC-27 and killing effect on hypoxic gastric cancer cells. At a concentration of 300 μm and more, trans-1,3-dilinolein kills gastric cancer cells significantly and the killing effect becomes more significant under hypoxic conditions.

4 Claims, 5 Drawing Sheets

APPLICATION OF TRANS-1,3-DILINOLEIN IN THE PREPARATION OF MEDICAMENTS FOR TREATING GASTRIC CANCER, STOMACHIC TONIC, HEALTH PRODUCTS AND FOODS

CROSS REFERENCE TO RELATED APPLICATIONS

This patent application claims the priority of Chinese Patent Application No. 202110026727.7, filed on Jan. 9, 2021, the disclosure of which is incorporated by reference herein in its entirety as part of the present application.

FIELD OF THE DISCLOSURE

The present disclosure belongs to the field of medicine and food, and specifically relates to an application of trans-1,3-dilinolein in the preparation of medicaments for treating gastric cancer, stomachic tonic, stomachic health products and functional foods.

BACKGROUND

Cancer has always been a great enemy of mankind. According to the latest statistics from the World Health Organization (http://gco.iarc.fr/today), only in 2018, there are 18 million cancer cases worldwide, and the number of deaths from cancer is over 9.5 million; in China, there are 4.2 million cancer cases, and the number of deaths from cancer is over 2.8 million. In particular, the number of gastric cancer patients and deaths in China has exceeded 40% of the incidence and deaths of gastric cancer worldwide. The early treatment for gastric cancer patients is mainly surgical treatment, of which the five-year survival rate can reach more than 80%. But it is regrettable that, the early diagnosis rate of gastric cancer in China is lower than 10%, and over 90% of patients have been in the advanced stage when they are detected, at which time the golden age of radical operation has been missed, and chemotherapy has to be adopted mostly. However, many chemicals fail to distinguish between normal gastric mucosal epithelial cells and gastric cancer cells and kill them all. Therefore, the exploration and discovery of anti-cancer active molecules capable of protecting normal gastric mucosal epithelial cells and killing gastric cancer cells at the same time are of great significance for the development of medicaments with spleen-strengthening and anti-cancer activities and great health products.

[2-hydroxy-3-[(9E,12E)-octadeca-9,12-dienoyl]oxypropyl](9E,12E)-octadeca-9,12-dienoate, also known as trans-1,3-dilinolein, has a chemical structural formula as shown below:

The CAS Number is 15818-46-9. No documents have reported that this compound has stomachic and anti-gastric cancer activities.

SUMMARY

The following presents a simplified summary of the invention to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

The present disclosure is intended to provide new uses of trans-1,3-dilinolein as medicaments and food. To realize such purposes, some embodiments the present disclosure employs the following technical schemes.

1. An application of trans-1,3-dilinoleinan in the preparation of medicaments for treating gastric cancer.
2. An application of trans-1,3-dilinolein in the preparation of stomachic tonic.
3. An application of trans-1,3-dilinolein in the preparation of health products with strengthening-stomach effects.
4. An application of trans-1,3-dilinolein in the preparation of functional foods with strengthening-stomach effects.
5. An application of trans-1,3-dilinolein as a food additive with strengthening-stomach effects.
6. An anti-gastric cancer medicament, including trans-1,3-dilinolein as the active pharmaceutical ingredient, and one or more pharmaceutically acceptable accessories.
7. A stomachic tonic, including trans-1,3-dilinolein as the active pharmaceutical ingredient, and one or more pharmaceutically acceptable accessories.
8. A stomachic health products, including trans-1,3-dilinolein as the strengthening-stomach active ingredient.
9. A functional food with strengthening-stomach effects, including trans-1,3-dilinolein with strengthening-stomach activity.

In some embodiments, the disclosure provides a method of treating at least one of gastric cancer and invigorating stomach in a subject in need thereof. The method includes administering to the subject a composition a including a therapeutically effective amount of trans-1,3-dilinolein, the chemical structural formula of which is shown as below:

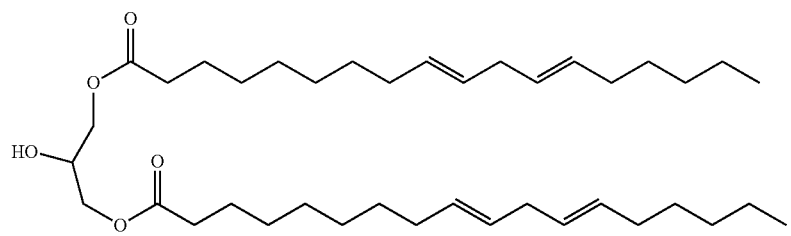

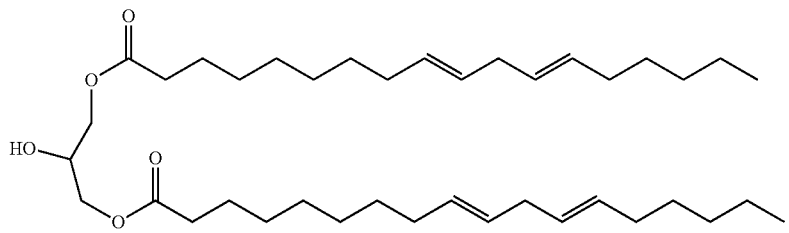

Optionally, the trans-1,3-dilinolein is used as an active pharmaceutical ingredient in a medicament for treating at least one of gastric cancer and invigorating stomach.

Optionally, the trans-1,3-dilinolein is used as the only active pharmaceutical ingredient in the medicament for treating at least one of gastric cancer and invigorating stomach.

Optionally, the treating gastric cancer means that the trans-1,3-dilinolein is used as an active pharmaceutical ingredient to inhibit proliferation activities of gastric cancer cells under a normal oxygen environment or a hypoxic environment, and the treating invigorating stomach means that the trans-1,3-dilinolein is used as an active pharmaceutical ingredient to promote proliferation activities of gastric mucosal epithelial cells under a normal oxygen environment or a hypoxic environment.

In other embodiments, the disclosure provides an anti-gastric cancer medicament, including trans-1,3-dilinolein as the active pharmaceutical ingredient and one or more pharmaceutically acceptable accessories. The chemical structural formula of the trans-1,3-dilinolein is shown as below:

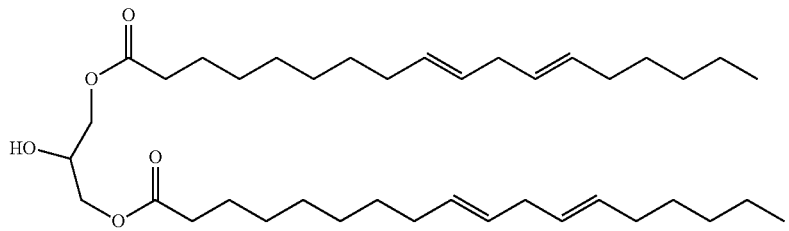

In further embodiments, the disclosure provides a stomachic health product for strengthening stomach activities, including trans-1,3-dilinolein as a stomachic active ingredient. The chemical structural formula of trans-1,3-dilinolein is shown as below:

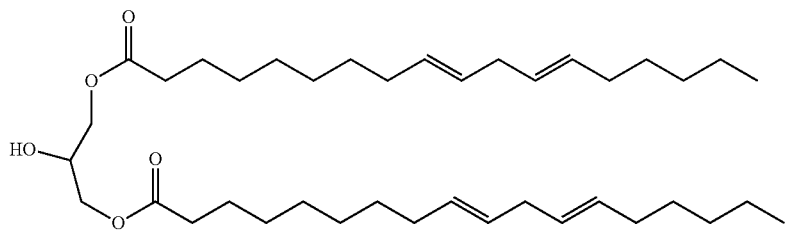

BRIEF DESCRIPTION OF THE DRAWINGS

Illustrative embodiments of the present disclosure are described in detail below with reference to the figures.

DETAILED DESCRIPTION

Figure 1:
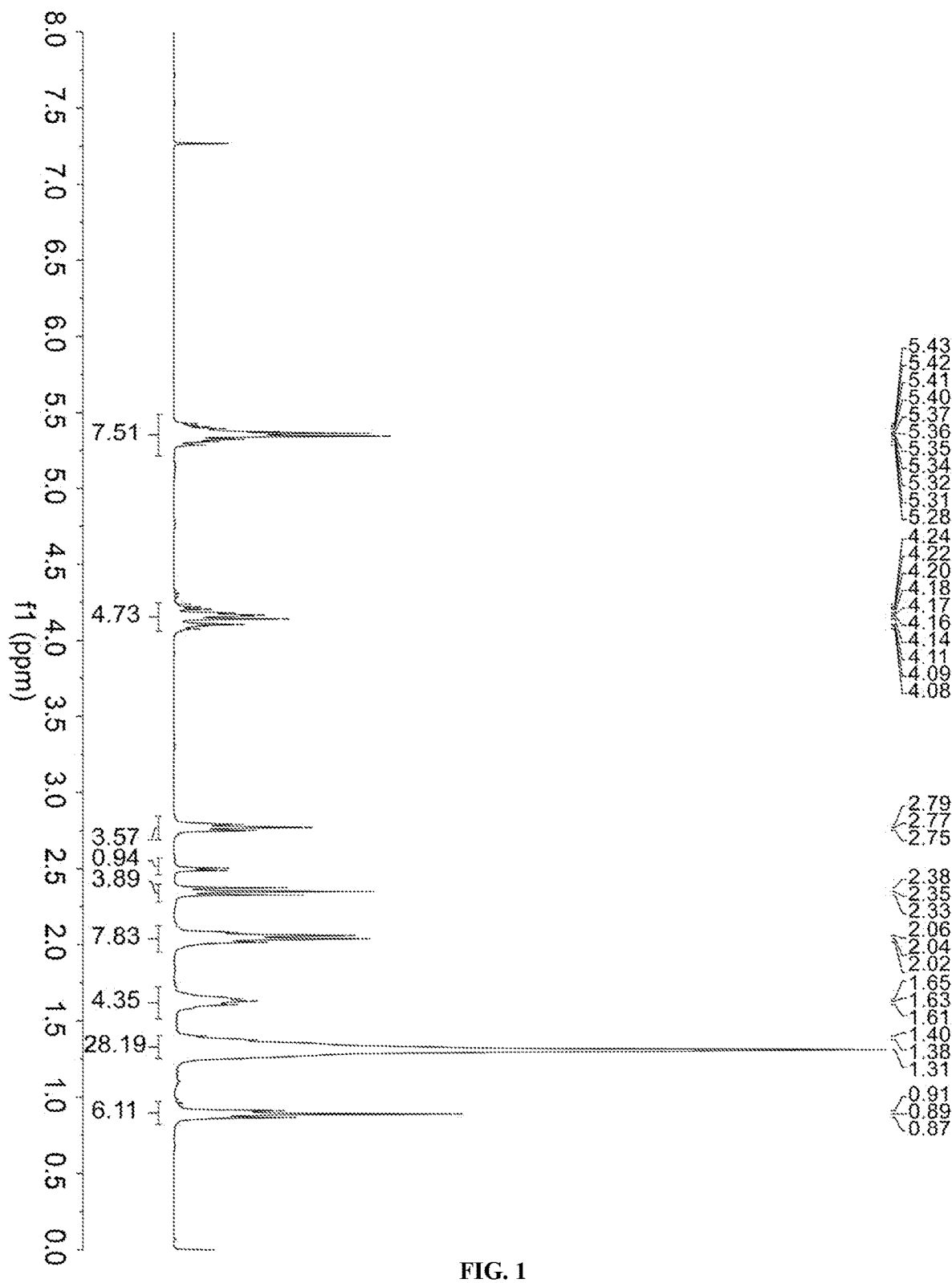
FIG. 1 shows a nuclear magnetic spectrum of 1,2-glycerol acetyl lactone.

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

The present disclosure will be further illustrated in detail in combination with the attached drawings and the following embodiments.

The trans-1,3-dilinolein of the present disclosure has the following chemical structural formula:

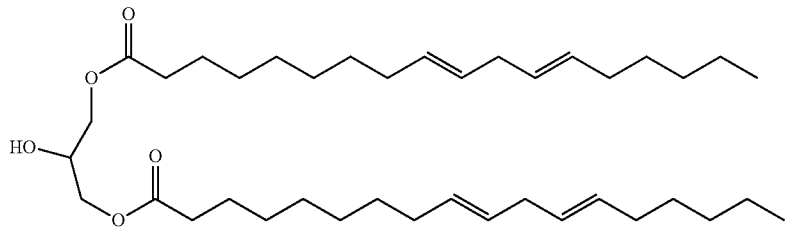

The present disclosure provides an application of trans-1,3-dilinolein in the preparation of medicaments for treating gastric cancer.

In some embodiments, the trans-1,3-dilinolein is used as the active pharmaceutical ingredient in the medicaments for treating gastric cancer.

In some embodiments, the trans-1,3-dilinolein is used as the only active pharmaceutical ingredient in the medicaments for treating gastric cancer.

The present disclosure also provides an anti-gastric cancer medicament, which may include trans-1,3-dilinolein as the active pharmaceutical ingredient, and one or more pharmaceutically acceptable accessories.

In some embodiments, the anti-gastric cancer medicament is a medicament that has an activity of inhibiting the proliferation of gastric cancer cells under normal oxygen and/or hypoxic environment.

In some embodiments, the dosage form of the anti-gastric cancer medicament may be tablets, granules, capsules, or other pharmaceutically acceptable dosage forms.

In some embodiments, the pharmaceutically acceptable accessories include fillers, binders, disintegrants, lubricants, glidants, correctives, colorants, and the like.

The present disclosure also provides an application of trans-1,3-dilinolein in the preparation of stomachic tonic.

In some embodiments, the trans-1,3-dilinolein is used as the active pharmaceutical ingredient in the stomachic tonic.

In some embodiments, the trans-1,3-dilinolein is used as the only active pharmaceutical ingredient in the stomachic tonic.

The present disclosure also provides a stomachic tonic, which may include trans-1,3-dilinolein as the active pharmaceutical ingredient, and one or more pharmaceutically acceptable accessories.

In some embodiments, the stomachic tonic is a medicament that has an activity of promoting the proliferation of gastric mucosal epithelial cells under normal oxygen and/or hypoxic environment.

In some embodiments, the dosage form of the stomachic tonic may be tablets, granules, capsules, or other pharmaceutically acceptable dosage forms.

In some embodiments, the pharmaceutically acceptable accessories include fillers, binders, disintegrants, lubricants, glidants, correctives, colorants, and the like.

Based on its excellent effect of promoting the proliferation of normal human gastric mucosal epithelial cell line GES-1 under normal oxygen and hypoxic conditions, trans-1,3-dilinolein may also be used to prepare health products with strengthening-stomach effects, and trans-1,3-dilinolein may be used as the food additive with strengthening-stomach effects to prepare functional foods with strengthening-stomach effects.

2,3-dihydroxypropyl (9E,12E)-9,12-octadecadienoate is a dihydroxy compound, and the two hydroxy groups are adjacent. To selectively introducing octadeca-9,12-diene onto the terminal hydroxy, the present disclosure also provides a method of preparing trans-1,3-dilinolein, which may include:

In the presence of 4-dimethylaminopyridine (DMAP) and triethylamine, 2,3-dihydroxypropyl (9E,12E)-9,12-octadecadienoate is reacted with (9E,12E)-9,12-octadecadienoyl chloride to get the trans-1,3-dilinolein.

In some embodiments, the using amount of 4-dimethylaminopyridine is 1-20% the mass of 2,3-dihydroxypropyl (9E,12E)-9,12-octadecadienoate.

In some embodiments, the using amount of 4-dimethylaminopyridine is 1%, 2%, 4%, 8%, 10%, 12%, 14%, 16%, 18%, 20% the mass of 2,3-dihydroxypropyl (9E,12E)-9,12-octadecadienoate, or an interval range composed of any two numerical values, e.g., 8-12%.

In some embodiments, the using amount of triethylamine is 0.5-5 times the mass of 2,3-dihydroxypropyl (9E,12E)-9,12-octadecadienoate.

In some embodiments, the using amount of triethylamine is 0.5 times, 1 time, 1.5 times, 2 times, 2.5 times, 3 times, 3.5 times, 4 times, 4.5 times, 5 times the mass of 2,3-dihydroxypropyl (9E,12E)-9,12-octadecadienoate, or an interval range composed of any two numerical values, e.g., 1.5-2 times.

In some embodiments, the molar ratio of 2,3-dihydroxypropyl (9E,12E)-9,12-octadecadienoate to (9E,12E)-9,12-octadecadienoyl chloride is controlled at 1:0.1-1:10.

In some embodiments, the molar ratio of 2,3-dihydroxypropyl (9E,12E)-9,12-octadecadienoate to (9E,12E)-9,12-octadecadienoyl chloride is 1:0.1, 1:0.5, 1:1, 1:1.5, 1:2, 1:3, 1:4, 1:6, 1:10, or an interval range composed of any two numerical values, e.g., 1:1-1:2.

The above reaction may be carried out in an inert solvent such as dichloromethane (DCM).

The above reaction may be carried out in an ice bath, and the reaction time may be controlled at 10-24 hours.

In some embodiments, the 2,3-dihydroxypropyl (9E,12E)-9,12-octadecadienoate may be prepared by a method including the following steps: (1) In the presence of a catalytic amount of acid, glycerin is reacted with acetone to get 1,2-glycerol acetyl lactone. (2) In the presence of 4-dimethylaminopyridine and dicyclohexylcarbodiimide (DCC), 1,2-glycerol acetyl lactone is reacted with trans-linoleic acid to get (2,2-dimethyl-1,3-dioxolan-4-yl)-methyl (9E,12E)-9,12-octadecadienoate. (3) (2,2-dimethyl-1,3-dioxolan-4-yl)-methyl (9E,12E)-9,12-octadecadienoate is hydrolyzed in the presence of an acid to get the 2,3-dihydroxypropyl (9E,12E)-9,12-octadecadienoate.

In some embodiments, the acid in step (1) is selected from p-toluene sulfonic acid.

In some embodiments, the using amount of p-toluene sulfonic acid is 0.01-0.1% the molar quantity of glycerin.

Optionally, the using amount of p-toluene sulfonic acid is 0.05% the molar quantity of glycerin.

In some embodiments, the temperature at which glycerin is reacted with acetone in step (1) is controlled at 50-100° C.

Optionally, the temperature at which glycerin is reacted with acetone is controlled at 70° C.

In some embodiments, the using amount of 4-dimethylaminopyridine in step (2) is 1-10% the mass of 1,2-glycerol acetyl lactone.

Optionally, the using amount of 4-dimethylaminopyridine is 4-6% the mass of 1,2-glycerol acetyl lactone.

In some embodiments, the using amount of dicyclohexylcarbodiimide in step (2) is 1-5 times the mass of 1,2-glycerol acetyl lactone.

Optionally, the using amount of dicyclohexylcarbodiimide is 3-4 times the mass of 1,2-glycerol acetyl lactone.

In the presence of dimethylformamide (DMF), trans-linoleic acid is reacted with sulfoxide chloride to get (9E, 12E)-9,12-octadecadienoyl chloride.

In some embodiments, trans-linoleic acid is reacted with an excessive amount of sulfoxide chloride.

Optionally, the using amount of sulfoxide chloride is 2-5 times the molar quantity of trans-linoleic acid.

The chemical structural formula of trans-linoleic acid is as below:

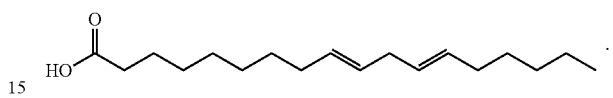

Embodiment 1

The synthetic route of trans-1,3-dilinolein is as below:

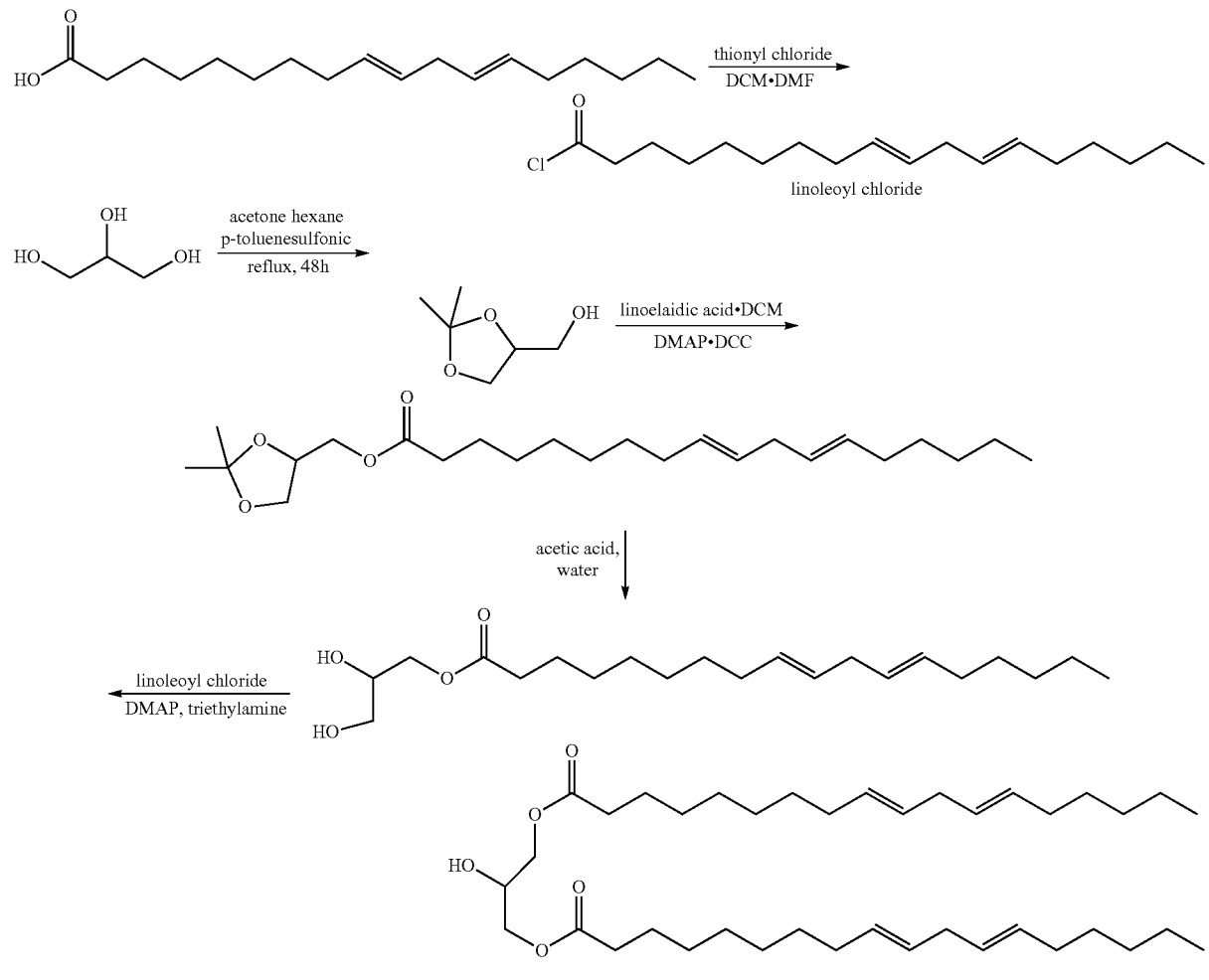

In some embodiments, the acid in step (3) is selected from acetic acid.

Optionally, the hydrolysis temperature in step (3) is controlled at 40-60° C.

In some embodiments, the (9E,12E)-9,12-octadecadienoyl chloride may be prepared by the following method:

The above synthesizing process is explained in more details as below.

(1) Synthesis of 1,2-glycerol acetyl lactone

Glycerin (40 mmol, 3.223 g) and p-toluene sulfonic acid (0.02 mmol, 0.004 g) are placed in a 100 ml round-bottom flask, and dissolved by adding acetone (31.5 mmol, 1.83 g), then hexane (11 ml) is added, and the temperature is set at 70° C. 1 ml acetone is added every 12 hours and reacted under such conditions for 48-60 hours. The reaction is detected by TLC. After the completion of the reaction, the solvent is removed by rotary evaporation under reduced pressure. And then isolation and purification are conducted through a silica gel column to get the compound 1,2-glycerol acetyl lactone (its chemical structural formula is

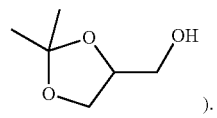
).

The nuclear magnetic spectrum of 1,2-glycerol acetyl lactone is shown in FIG. 1.

(2) Synthesis of (2,2-dimethyl-1,3-dioxolan-4-yl)-methyl(9E,12E)-9,12-octadecadienoate 1,2-glycerol acetyl lactone (1.07 mmol, 0.141 g), trans-linoleic acid (1.07 mmol, 0.300 g) and DMAP (0.06 mmol, 0.007 g) are placed in a 50 mL round-bottom flask and dissolved by adding dichloromethane (6 mL). DCC (2.14 mmol, 0.441 g) is then dissolved in 4 mL dichloromethane, and dropwise added into the round-bottom flask charged with 1,2-glycerol acetyl lactone in an ice bath (0° C.), reacted at room temperature overnight and detected by TLC. After the completion of the reaction, insoluble solid is removed by filtration, and washed with petroleum ether for 3-5 times. The filtrate is collected and rotary-evaporated under reduced pressure, then isolated and purified through a silica gel column to get the compound (2,2-dimethyl-1,3-dioxolan-4-yl)-methyl(9E,12E)-9,12-octadecadienoate (its chemical structural formula is:

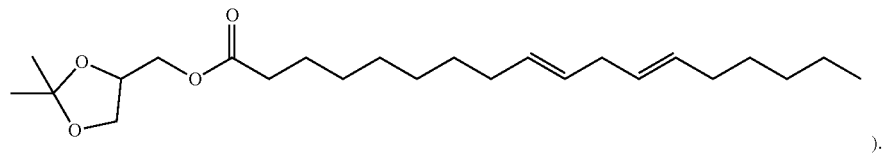 [SMILES: CCCCC/C=C/C/C=C/CCCCCCCC(=O)OCC1COC(C)(C)O1]
).

Figure 2:
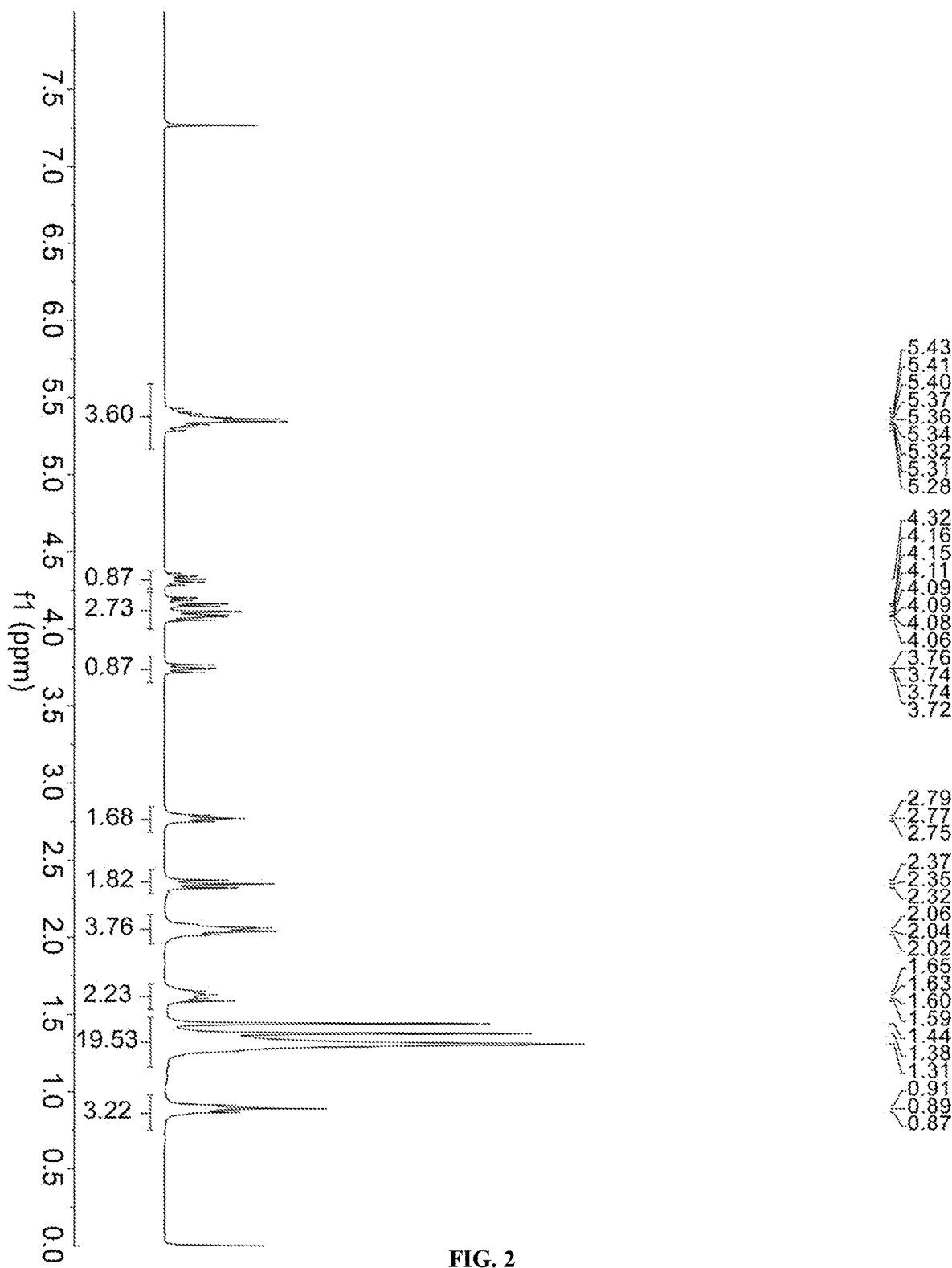
FIG. 2 shows a nuclear magnetic spectrum of (2,2-dimethyl-1,3-dioxolan-4-yl)-methyl(9E,12E)-9,12-octadecadienoate.

The nuclear magnetic spectrum of (2,2-dimethyl-1,3-dioxolan-4-yl)-methyl(9E,12E)-9,12-octadecadienoate is shown in FIG. 2.

(3) Synthesis of 2,3-dihydroxypropyl (9E,12E)-9,12-octadecadienoate (2,2-dimethyl-1,3-dioxolan-4-yl)-methyl(9E,12E)-9,12-octadecadienoate (0.76 mmol, 0.301 g) is placed in a 25 ml round-bottom flask and dissolved by adding 2880 ul glacial acetic acid and 720 ul water. The reaction is refluxed by heating at 50° C. for 7-12 hours and detected by TLC. After the completion of the reaction, they are extracted with ethyl acetate for three times. The resulting organic phase is washed twice with a saturated NaCl solution and dried over anhydrous $Na_2SO_4$. The filtrate is collected and rotary-evaporated under reduced pressure, then isolated and purified through a silica gel column to get the compound 2,3-dihydroxypropyl (9E,12E)-9,12-octadecadienoate.

(4) Synthesis of trans-1,3-dilinolein

Trans-linoleic acid (0.423 mmol, 0.118 g), sulfoxide chloride (1.69 mmol, 0.201 g, 120 ul, 4 eq) are placed in a 50 ml round-bottom flask, and dissolved by adding 6 ml dichloromethane, and then three drops of DMF is additionally added. After reaction for 12 hours, it is detected by TLC. After the completion of the reaction, the solvent is removed by rotary evaporation. 6 ml dichloromethane is added for rotary evaporation for three times to remove off sulfoxide chloride to get the compound (9E,12E)-9,12-octadecadienoyl chloride (its chemical structural formula is:

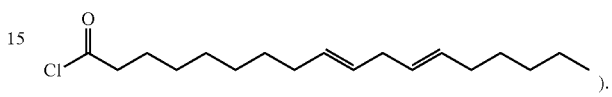
).

Figure 3:
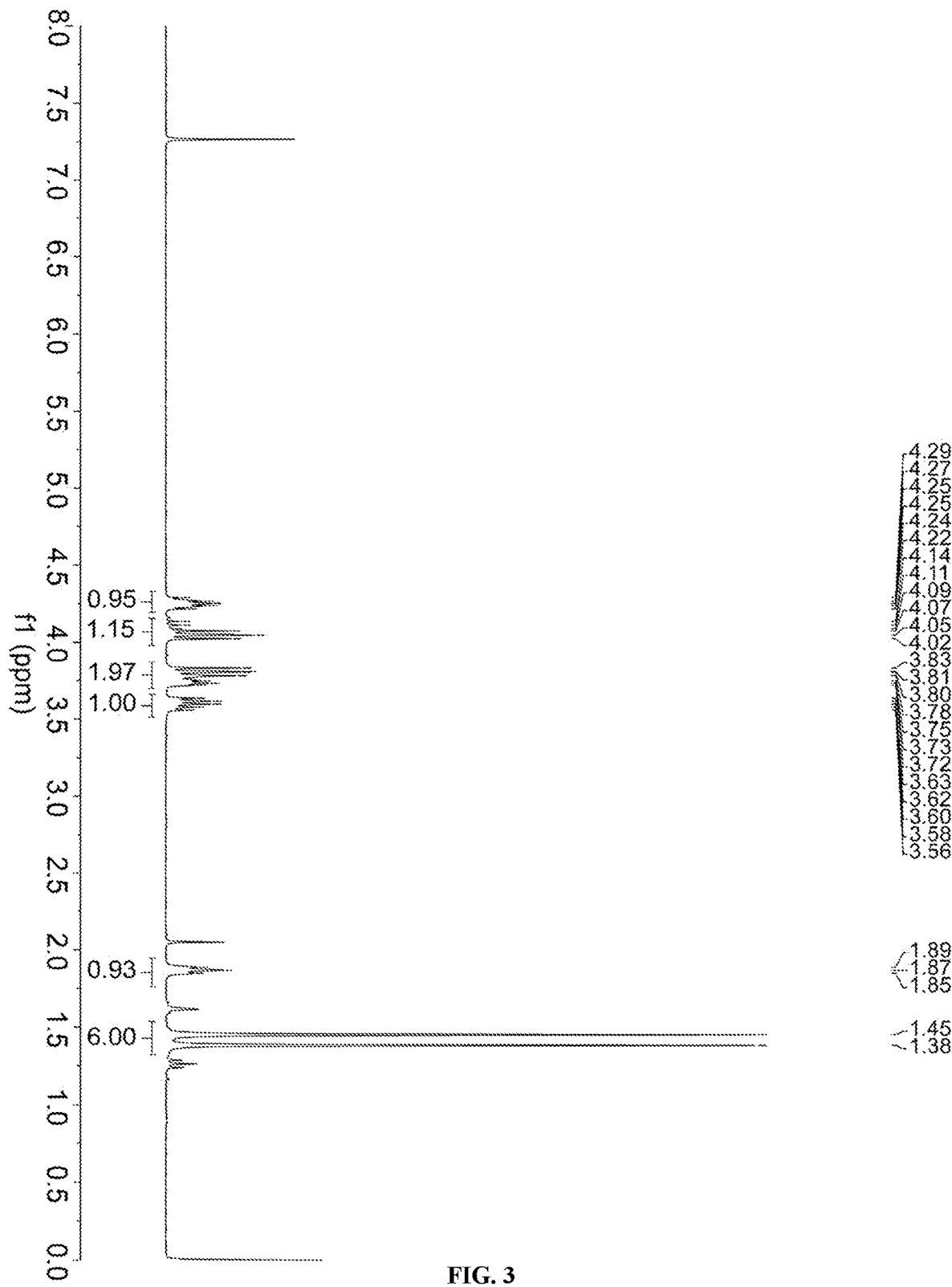
FIG. 3 shows a nuclear magnetic spectrum of trans-1,3-dilinolein.

It is dissolved in 2 ml dichloromethane and added into a 50 ml reaction flask charged with 2,3-dihydroxypropyl (9E,12E)-9,12-octadecadienoic acid (0.282 mmol, 0.100 g). DMAP (10%, 10 mg) and triethylamine (1.805 mmol, 0.183 g, 248 ul, 6.4 eq) are added into 2-4 ml dichloromethane and dropwise added into the 50 ml reaction flask in an ice bath (0° C.). After reaction for 12 hours, the reaction is detected by TLC. After the completion of the reaction, the solvent is removed by rotary evaporation. Then isolation and purification are conducted through a silica gel column to get the compound trans-1,3-dilinolein, with a yield of 50%. The nuclear magnetic spectrum of trans-1,3-dilinolein is shown in FIG. 3.

Embodiment 2 Cell Model Experiment of Trans-1,3-Dilinolein

Cell Culture

At 37° C. and 5% $CO_2$, human gastric cancer cell line HGC-27 cells and human gastric mucosal epithelial cell line GES-1 cells (coming from China Center for Type Culture Collection (Wuhan, China)) are respectively cultured in RPMI Medium Modified (Hyclone, SH30809.01) and Dulbecco's Modified Eagle's Medium-high glucose (Sigma, D6429), in which 10% fetal calf serum (Gibco, 10270-106) and 1% penicillin-streptomycin (Gibco, 15140-122) are supplemented.

Determination of Cell Activity

The cytotoxicity of HGC-27 cells by trans-1,3-dilinolein is determined. 5000 cells are plated in a 96-well plate, and each well is added with 100 μL medium. 12 hours after cell attachment, each well is given 100 μL normal medium that contained different concentrations (0 μM, 50 μM, 100 μM, 200 μM, 300 μM, 400 μM, 500 μM) of trans-1,3-dilinolein and had been preheated, and cultured in incubators under the conditions of 5% $CO_2$, 37° C., normal oxygen and 1% oxygen respectively for 48 hours. The medium in each well is drawn, and serum-free medium is added into each well to formulate 60 μL MTS (Promega) at ⅙ the initial concentration, which are correspondingly incubated in incubators under the conditions of 5% $CO_2$, 37° C., normal oxygen and 1% oxygen for 2 hours. The absorbance at 490 nm is determined with a microplate reader (Thermo Scientific).

The cytotoxicity of GES-1 cells by trans-1,3-dilinolein is determined. 10000 cells are plated in a 96-well plate, and each well is added with 100 μL medium. 12 hours after cell attachment, each well is given 100 μL normal medium that contained different concentrations (0 μM, 6.25 μM, 12.5 μM, 25 μM, 50 μM, 100 μM, 200 μM, 400 μM, 800 μM, 1000 μM) of trans-1,3-dilinolein and had been preheated, and cultured in incubators under the conditions of 5% $CO_2$, 37° C., normal oxygen and 1% oxygen respectively for 48 hours. The medium in each well is drawn, and serum-free medium is added into each well to formulate 60 μL CCK8 (ABMole BioScience) at 1/11 the initial concentration, which are correspondingly incubated in incubators under the conditions of 5% $CO_2$, 37° C., normal oxygen and 1% oxygen for 40 minutes. The absorbance at 450 nm is determined with a microplate reader (Thermo Scientific).

Statistics

Two-side Student's t-test is conducted by using EXCEL to determine the statistical significance of two groups of measurements. P value<0.05 is considered to be statistically significant. Unless otherwise specified, all data are expressed as mean ±standard deviation.

Experimental Results

Figure 4A:
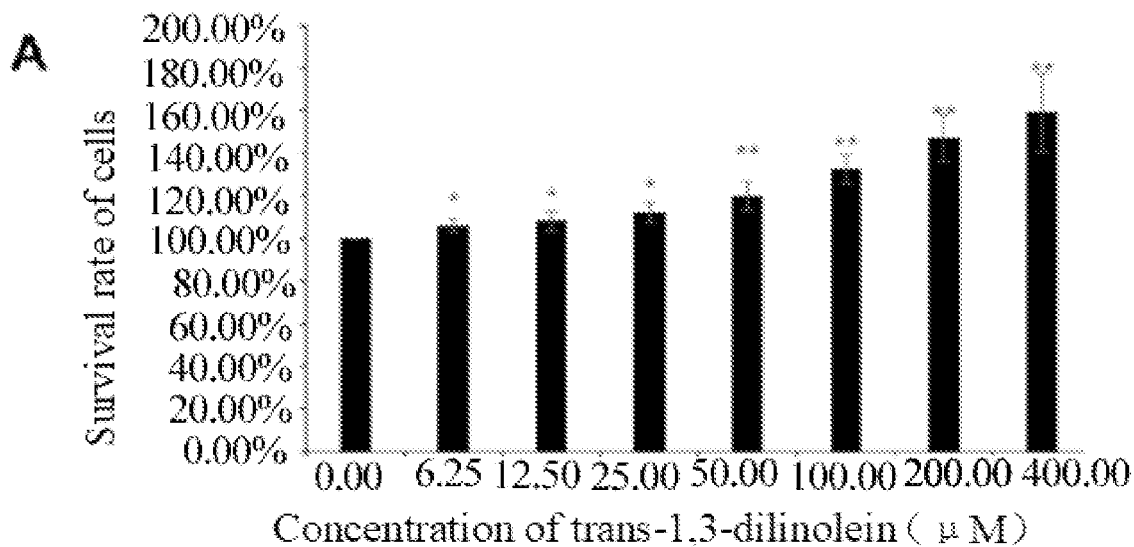
FIG. 4A shows stomachic effect of trans-1,3-dilinolein promoting the proliferation of human normal gastric mucosal epithelial cells under normal oxygen conditions.
Figure 4B:
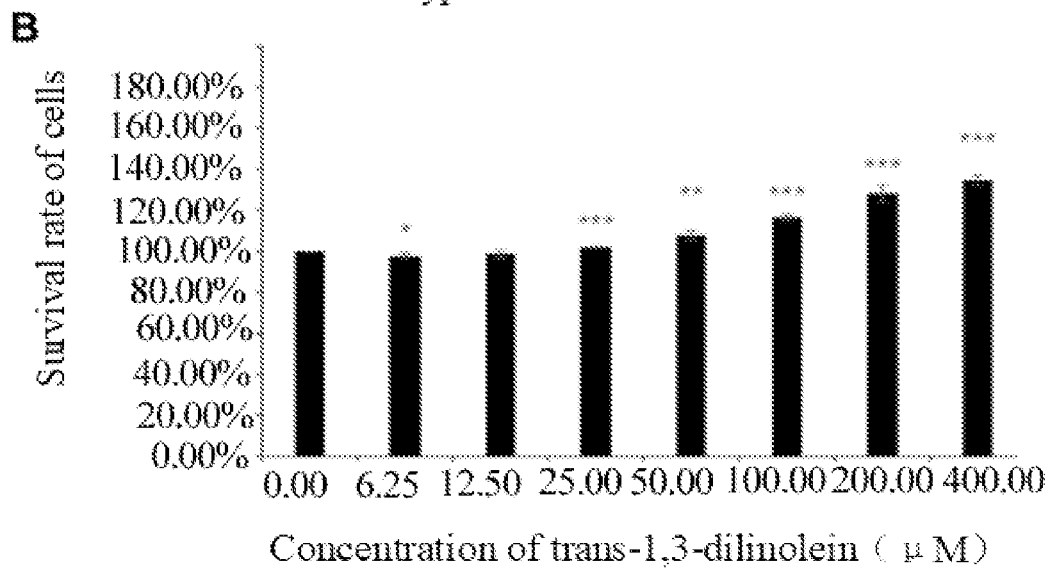
FIG. 4B shows stomachic effects of trans-1,3-dilinolein promoting the proliferation of human normal gastric mucosal epithelial cells under hypoxic conditions.
Figure 4C:
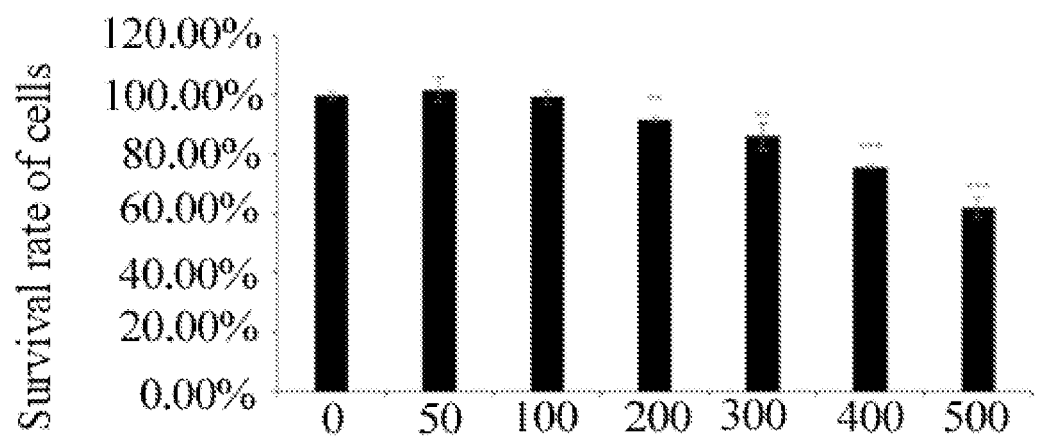
FIG. 4C shows anti-cancer effects of trans-1,3-dilinolein inhibiting the proliferation of human gastric cancer cells under normal oxygen conditions.
Figure 4D:
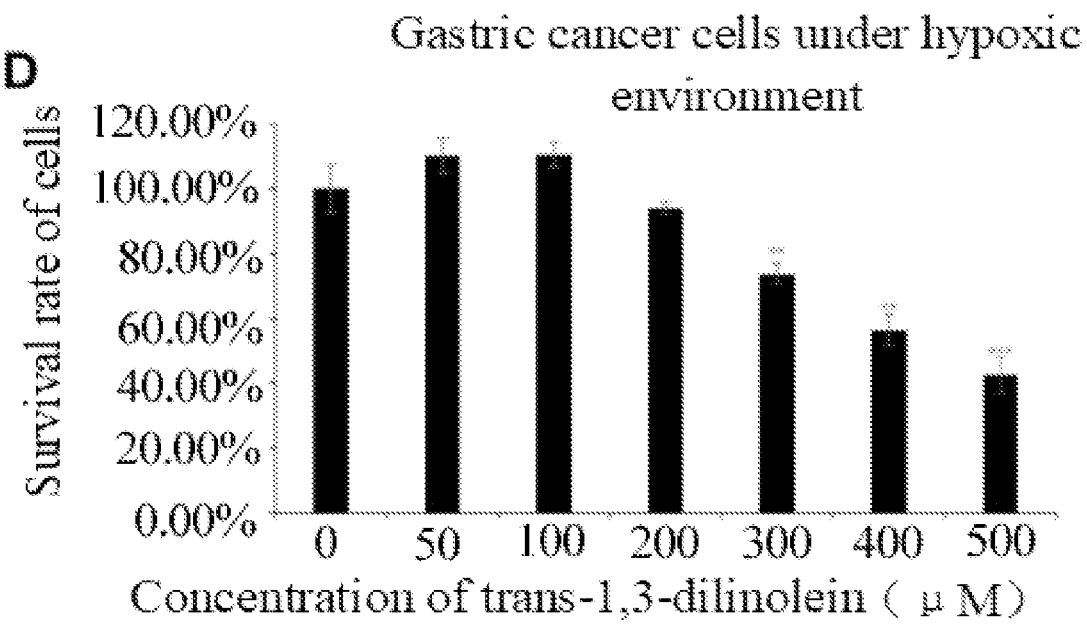
FIG. 4D shows anti-cancer effects of trans-1,3-dilinolein inhibiting the proliferation of human gastric cancer cells under hypoxic conditions.

The results are shown in FIGS. 4A-4D, trans-1,3-dilinolein in a range of 25 μM to 400 μm has promotion effects on the proliferation of human gastric mucosal epithelial cell line GES-1 under normal oxygen and hypoxic conditions (FIG. 4A and FIG. 4B). Trans-1,3-dilinolein has concentration-dependent killing effect on human gastric cancer cell line HGC-27 and has stronger killing effect on hypoxic gastric cancer cells (FIG. 4C and FIG. 4D). It should be noted that at a concentration of 300 μm and more, trans-1,3-dilinolein kills gastric cancer cells significantly and the killing effect is more significant under hypoxic conditions, at the same time, it may significantly promote the proliferation of normal gastric mucosal epithelial cells. The above results show that, trans-1,3-dilinolein is a potential excellent stomachic and anti-cancer active ingredient that may not only protect normal gastric mucosal cells, but also kill gastric cancer cells.

Various embodiments of the disclosure may have one or more of the following effects. In some embodiments, trans-1,3-dilinolein may significantly promote the proliferation of normal gastric mucosal epithelial cells and trans-1,3-dilinolein may be used to prepare stomachic and anti-cancer medicaments capable of protecting normal gastric mucosal cells and killing gastric cancer cells.

It should be noted that: the foregoing is only preferable implementation of the present disclosure, rather than being used to limit the present disclosure. Although the present disclosure has been illustrated in detail with reference to the foregoing embodiments, modifications may be made to the technical schemes set forth in the above embodiments, or equivalent replacements may be made to some of the technical features by those skilled in the art. Any modifications, equivalent replacements, and improvements made within the spirit and principle of the present disclosure should all be covered within the protection scope of the present disclosure.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A method of treating gastric cancer in a subject in need thereof, the method comprising administering to the subject a composition comprising a therapeutically effective amount of trans-1,3-dilinolein, the chemical structural formula of which is shown as below:

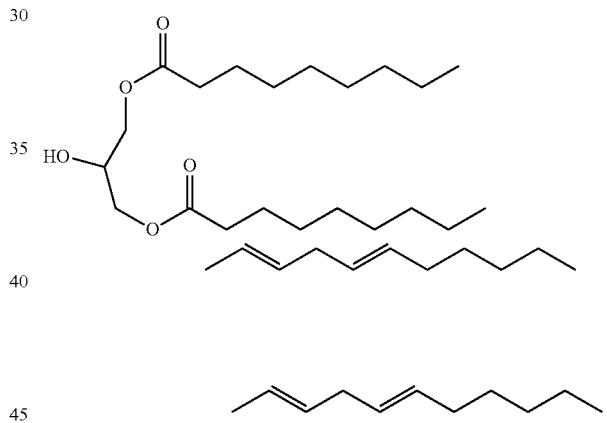

2. The method according to claim 1, wherein the trans-1,3-dilinolein is used as an active pharmaceutical ingredient in a medicament for treating gastric cancer.

3. The method according to claim 2, wherein the trans-1,3-dilinolein is used as the only active pharmaceutical ingredient in the medicament for treating gastric cancer.

4. The method according to claim 1, wherein
the treating gastric cancer means that the trans-1,3-dilinolein is used as an active pharmaceutical ingredient to inhibit proliferation activities of gastric cancer cells under a normal oxygen environment or a hypoxic environment.

* * * * *